US006146658A

United States Patent [19]
Bosslet et al.

[11] Patent Number: 6,146,658
[45] Date of Patent: *Nov. 14, 2000

[54] PRODRUGS, THEIR PREPARATION AND USE AS PHARMACEUTICALS

[75] Inventors: Klaus Bosslet; Jörg Czech, both of Marburg; Dieter Hoffmann, Marburg-Elnhausen; Cenek Kolar, Marburg, all of Germany; François Tillequin, Paris, France; Jean-Claude Florent, Les Ulis, France; Michel Azoulay; Claude Monneret, both of Paris, France; Jean-Claude Jacquesy, Buxerolles, France; Jean-Pierre Gesson, Chansseneuil du Poitou, France; Michel Koch, La Celle Saint Cloud, France

[73] Assignee: Hoechst Aktiengesellschaft, Frankfurt am Main, Germany

[*] Notice: This patent is subject to a terminal disclaimer.

[21] Appl. No.: 08/859,084

[22] Filed: May 20, 1997

Related U.S. Application Data

[60] Continuation of application No. 08/449,021, May 24, 1995, which is a division of application No. 08/140,825, Oct. 25, 1993, abandoned.

[30] Foreign Application Priority Data

Oct. 27, 1992 [DE] Germany ............................. 42 36 237

[51] Int. Cl.[7] ............................. A23B 4/03; A61K 31/70; A61K 38/16
[52] U.S. Cl. ............................... 424/450; 514/8; 514/23; 514/25; 514/53; 514/54
[58] Field of Search ........................... 536/4.1, 6.4, 17.2; 424/450; 514/23, 25, 53, 54, 8

[56] References Cited

U.S. PATENT DOCUMENTS

| | | | |
|---|---|---|---|
| 4,265,885 | 5/1981 | Bargiotti et al. | 514/34 |
| 4,279,992 | 7/1981 | Boguslaski et al. | 435/7.72 |
| 4,481,195 | 11/1984 | Rubin | 514/25 |
| 4,975,278 | 12/1990 | Senter et al. | 424/178.1 |
| 5,013,556 | 5/1991 | Woodle et al. | 424/450 |
| 5,049,549 | 9/1991 | Kolar et al. | 514/34 |
| 5,122,368 | 6/1992 | Greenfield et al. | 424/85.2 |
| 5,132,416 | 7/1992 | Tietze et al. | 536/117 |
| 5,137,877 | 8/1992 | Kaneko et al. | 541/25 |
| 5,213,804 | 5/1993 | Martin et al. | 424/450 |
| 5,387,578 | 2/1995 | Angelucci et al. | 514/21 |
| 5,433,955 | 7/1995 | Bredehorst et al. | 424/94.3 |
| 5,434,247 | 7/1995 | Matteucci et al. | 530/228 |
| 5,561,119 | 10/1996 | Jacquesy et al. | 514/34 |

FOREIGN PATENT DOCUMENTS

| | | |
|---|---|---|
| 2021911 | 1/1991 | Canada . |
| 2035385 | 8/1991 | Canada . |
| 0410366A1 | 1/1991 | European Pat. Off. . |
| 0441218A2 | 8/1991 | European Pat. Off. . |
| 1541436 | 2/1979 | United Kingdom . |
| WO 81/01145 | 4/1981 | WIPO . |
| WO 88/07378 | 10/1988 | WIPO . |
| WO92/19639 | 11/1992 | WIPO . |

OTHER PUBLICATIONS

R. Duncan et al., "Preclinical evaluation of polymer–bound doxorubicin," J. Controlled Release, vol. 19, Nos. 1/3, (Mar. 1992), pp. 331–346.

Y. Ohya et al., "Synthesis and cytotoxic activity of doxorubicin bound to poly($\alpha$–malic acid) via ester or amide bonds," Macromol. Chem., vol. 193, No. 8, (Aug. 1992), pp. 1881–1887.

V. Subr et al., "Polymers containing enzymatically degradable bonds, XII. Effect of spacer structure on the rate of release of daunomycin and adriamycin from poly[N–(2–hydroxypropyl)–methacrylamide]copolymer drug carriers in vitro and antitumour activity measured in vivo," J. Controlled Release, vol. 18 (1992), pp. 123–132.

"Sterically stabilized liposomes: Improvements in pharmacokinetics and antitumor therapeutic efficacy", Papahadiopoulos, et al., Proc. Natl. Acad. Sci. USA, 88:11460–11464 (1991).

"A Novel Method in the Induction of Reliable Experimental Acute and Chronic Ulcerative Colitis in Mice", Okayasu, et al., Gastroenterology 98:694–702 (1990).

"Possible in Situ Activation of Mycophenolic Acid by $\beta$–Glucuronidase", Sweeney, et al., Cancer Research 31:477–478 (1971).

"Therapeutic Trial Of Aniline Mustard In Patients With Advanced Cancer", Young, et al., Cancer 38:1887–1895 (1976).

"5–Fluorouracil O–$\beta$–D–Glucuronide As A Newly Synthesized Chemically Modified, Nontoxic Anticancer Drug", Baba, et al., Gann 69:283–284 (1978).

"A Novel Connector Linkage Applicable in Prodrug Design", Carl, et al., Journal of Medicinal Chemistry 24(5):479–480 (1981).

"Selective iodination and cytotoxicity of tumor cells with an antibody–enzyme conjugate", Philpott, et al., Surgery 74(1):51–58 (1973).

"Affinity Cytotoxicity of Tumor Cells with Antibody–Glucose Oxidase Conjugates, Peroxidase, and Arsphenamine", Philpott et al., Cancer Research 34:2159–2164 (1974).

"Molecular and functional characterisation of a fusion protein suited for tumour specific prodrug activation", Bosslet, et al., Br. J. Cancer 65: 234–238 (1992).

"N–(–D–Glycopyranosyl)–Benzyloxycarbonyl Daunorubicine Pro–Prodrugs Synthesis and enzymatic behaviour", Florent, et al., Int. Carbohydr. Symp. Paris, p. 297 (1992).

"N–(–D–Glycopyranosyl)–Nitrobenzyloxycarbonyl Daunorubicine Pro–Prodrugs and enzyme–catalysed hydrolysis", Gesson., et al., Int. Carbohydr. Symp. Paris, p. 298 (1992).

(List continued on next page.)

Primary Examiner—Elli Peselev
Attorney, Agent, or Firm—Finnegan, Henderson, Farabow, Garrett & Dunner, L.L.P.

[57] ABSTRACT

Glycosyl-spacer-drugs compounds (prodrugs), their preparation and their use as pharmaceuticals are described.

8 Claims, No Drawings

OTHER PUBLICATIONS

"N-(-D-Glycopyranosyl)-Chlorobenzyloxycarbonyl Daunorubicine Pro–Prodrugs and their enzymatic cleavage", Andrianomenjanahary, et al., Int. Carbohydr. Symp. Paris, p. 299 (1992).

"A modified mouse air pouch model for evaluating the effects of compounds on granuloma induced cartilage degradation", Bottomley, et al., Br. J. Pharmacol. 93:627–635 (1988).

"Immunosuppressive Activity of 15–Deoxyspergualin (15–DOS) on Various Models of Rheumatoid Arthritis", Schorlemmer, et al., Drugs Exptl. Clin. Res. XVII (10/11):471–483 (1991).

"Stimulation of Cell–Mediated Immunity by Bestatin Correlates with Reduction of Bacterial Persistence in Experimental Chronic *Salmonella typhimurium* Infection", Dickneite, et al., Infection and Immunity 44(1): 168–174 (1984).

Therapeutic Effects of 15–Deoxyspergualin In Acute And Chronic Relapsing Experimental Allergic Encephalomyelitis (EAE) As Models For Multiple Sclerosis (MS), Schorlemmer, et al., Drugs Exptl. Clin. Res. XVII(10/11): 461–469 (1991).

"Curative Effects of 15–Deoxyspergualin On Murine Systemic Lupus Erythematosus–Like Disease In MRL/1 Autoimmune Mice", Schorlemmer, et al., Int. J. Immunotherapy VII(4):169–180 (1991).

"Immunobiochemical and Molecular Biologic Characterization of the Cell Proliferation–associated Nuclear Antigen That Is Defined By Monoclonal Antibody Ki–67", Gerdes, et al., American Journal of Pathology 138(4):867–873 (1991).

"Interleukin 1 (IL–1) Gene Expression, Synthesis, and Effect of Specific IL–1 Receptor Blockade in Rabbit Immune Complex Colitis", Cominelli et al., J. Clin. Invest. 86:972–980 (1990).

PRODRUGS, THEIR PREPARATION AND USE AS PHARMACEUTICALS

This is a continuation of application Ser. No. 08/449,021, filed May 24, 1995, which is a division of application Ser. No. 08/140,825, filed Oct. 25, 1993, abandoned.

The invention relates to glycosyl-spacer-drug compounds (prodrugs), to the preparation thereof and to the use thereof as pharmaceuticals.

The therapy of malignant tumors, inflammatory diseases, or autoimmune diseases is, besides the inadequate efficacy of the therapeutics, usually associated with severe side effects. This deficiency can be mainly explained by the fact that the in vivo selectivity of the drugs used is too low. Thus, in many cases, the favorable in vitro pharmacological properties of the drugs cannot be confirmed in vivo.

Scientists have been concerned with this problem for many years, although without extensive success. One direction of research was concerned with the preparation and use of substances which are metabolized in viva to prodrugs which are subsequently cleaved site-specifically by enzymes to give the drugs. Thus, Sweeney and coworkers (Cancer Research 31, 477–478 1971) used mycophenolic acid, which is metabolized in viva to inert mycophenolic acid glucuronide, for the treatment of malignant tumors in animals. The observed effects on tumor growth were explained by the authors by enzymatic elimination of glucuronic acid by glucuronidase present outside the cells of the tumor, i.e. on the tumor cell membrane, followed by uptake of mycophenolic acid into the tumor cells. Attempts of therapy based on an identical concept were carried out by Young et al. (Cancer 38, 1887–1895, 1976) with aniline mustard in a clinical trial. They treated tumor patients whose tumors were tested for high p-glucuronidase levels with aniline mustard which, according to their hypothesis, ought to undergo hydroxylation in the liver followed by glucuronidation and be cleaved on the tumor by glucuronidase to toxic hydroxyaniline mustard. However, the therapeutic results were rather disappointing.

Another direction of research went one step further and entailed chemical preparation of, for example, aniline mustard methyl glucuronate or 6-mercaptopurine glucuronide. However, these prodrugs showed only a low degree of detoxification, which stood in the way of in vivo use. More favorable properties were shown by 5-fluorouracil O-p-D-glucuronide (FUOG) or 5-fluorouracil N-glucuronide (FUNG), compounds from a Japanese research group (Baba et al., Gann, 69, 283–284, 1978). The glucuronidation of 5-fluorouracil increased the LD50 from 200 mg/kg for 5-FU to 5,000 mg/kg for the corresponding glucuronide. However, a distinct effect was obtained only with FUOG after ten i.v. administrations and glucose acidification in the treatment of a mouse mammary carcinoma. However, it must be emphasized here that the treatment was started as early as 24 hours after implantation of a piece of tumor, a time at which it is certainly not yet possible to speak of an established tumor. Probably caused by potential tissue damage during the implantation, lysosomal glucuronidase was released in the tumor and, combined with the pH reduction associated with glucose treatment, led to in vivo activity. The relevance of this model for the clinical situation appears very doubtful, however. The fact that to date no therapeutic agent has resulted from these compounds indicates the low in vivo activity of the compounds.

Katzenellenbogen's research group (WO 81/01145) expected an improvement in the activity of prodrugs from the synthesis of peptide-spacer-drugs in place of glucuronyl-drugs. The activating enzymes intended to be used in this case are tumor-associated fibrinolytic or coagulating proteases such as, for example, plasmin or plasminogen activators. In vivo pharmacological activity was not shown either for the doxorubicin- or arabinosylcytosine-spacer-peptides described in WO. 81/01145 in the Journal of Medicinal Chemistry, 24, 479–480 (1981) and which can be activated in vitro by proteases. The lack of selective in vivo activity of these compounds can be explained given the background of our current knowledge about the ubiquitous extracellular occurrence of the abovementioned proteases in the human body.

Despite a large number of indications in the literature cited above about the not very successful use of prodrugs containing glucuronic acid, even in combination with glucose acidification (Baba, T. et al., Gann 69, 283–284, 1978), Rubin obtained in 1984 a U.S. Pat. No. 4,481,196) in which he proposes the use of glucuronic acid-drug compounds after acidification of the tumor and alkalinization of the normal tissue: It appears that no therapeutic agents which can be used with clinical success have emerged as yet from this invention.

In addition, butyric acid prodrugs which can be cleaved by esterases have been described. However, it has emerged that the therapeutic effects of the butyric acid liberated from the prodrugs in vivo are inferior to those of a standard cytostatic (cisplatin).

All the studies discussed so far are based on activation of prodrugs by endogenous enzymes. However, the in vivo therapeutic effects which can be achieved with this principle appear not to be superior to standard chemotherapy.

Independently of the direction of research described previously (prodrug activation by endogenous enzymes) there was development of a new direction of research which attempted, after prelocalization of xenogeneic antibody-enzyme conjugates in the target tissue, to cleave prodrugs selectively to cytotoxic drugs in the target tissue (Philpott et al., Surgery 74, 51, 1973; Cancer Res. 34, 2159, 1974). Bagshawe (WO 88/07378) proposed, based on the work of Philpott, the use of xenogeneic antibody-enzyme conjugates in combination with prodrugs for the treatment of tumors. He used mouse monoclonal antibodies chemically coupled to bacterial carboxypeptidase G2 as antibody-enzyme conjugate and glutamyl mustard as prodrug. Senter (U.S. Pat. No. 4,975,278) describes combination of antibody-enzyme conjugates composed of mouse monoclonal antibodies chemically bonded to alkaline phosphatase or penicillin V amidase with etoposide phosphate and N-(p-hydroxyphenoxyacetyl)adriamycin or prodrugs. Both systems (Bagshawe and Senter) have the disadvantage that the antibody-enzyme conjugates used are xenogeneic and thus highly immunogenic. This means that there is probably no possibility of employing them repeatedly on the same patient in a plurality of therapy cycles, In addition, the Senter system has the disadvantage that phosphatases occur in considerable quantity in human blood, which means that there is systemic activation of the prodrug.

As a result of these shortcomings, Bosslet et al. (Br. J. Cancer 65, 234–238, 1992) prepared a fusion protein which is composed of the humanized F(ab')2 fragment of an anti-CEA antibody and of human p-glucuronidase and which is enzymatically active, has tumor selectivity, is able to cleave glucuronyl-drugs (Florent et al., Int. Carbohydr. Symposium p. 297, Abstract A262, Paris, 1992; Gesson et al., Int. Carbohydr. Symposium p. 298, Abstract A263, Paris, 1992; Andrianomenjanahary et al., Int. Carbohydr. Symposium p. 299, Abstract A264, Paris, 1992) and, according to the current state of knowledge, has only little or no immunogenicity.

During studies on the synthesis and in vivo pharmacological testing of compounds which were intended to be optimally cleaved from this fusion protein, we have unexpectedly found substances which are cleaved very efficiently in tumors with a marked proportion of disintegrating cells, in inflammatory processes and in autoimmune diseases without previous administration of the fusion protein.

In this case, the compounds are activated by enzymes which in the healthy individual occur principally inside cells but which under the abovementioned pathophysiological conditions have a local extracellular occurrence.

These compounds have the general formula glycosyl-spacer-drug wherein the glycosyl radical and spacer can be cleaved off the drug under physiological or pathophysiological conditions. The properties of these compounds are such that, in general, the poly-, oligo- or monoglycosyl radical is cleaved off by enzymatic hydrolysis and then the spacer is spontaneously cleaved off by chemical hydrolysis. Drug means a chemical substance with biological effect, especially a pharmaceutical agent, as well as the derivatives thereof obtained by introducing additional hydroxyl, amino or imino groups.

The invention relates to compounds of this type and to the use thereof.

The invention relates in particular to glycosyl-spacer-drug compounds of the formula I

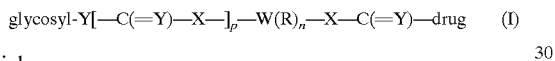

glycosyl-Y[—C(=Y)—X—]$_p$—W(R)$_n$—X—C(=Y)—drug  (I)

in which
glycosyl is a poly-, oligo- or monosaccharide which can be cleaved off enzymatically, W is an aromatic or heteroaromatic or aliphatic group with conjugated double bonds or an amino-acid derivative radical which cyclizes after elimination of the glycosyl radical, preferably having 5–20 carbon atoms and 0–4 heteroatoms, where heteroatom means N, O or S, to which the substituents R can be bonded, where R are, independently or identically, H, methyl, methoxy, carboxyl, methyloxycarbonyl, CN, hydroxyl, nitro, fluorine, chlorine, bromine, sulfo, sulfamoyl or (C1–4)-alkylsulfamoyl and p is 0 or 1, n is an integer, X is O, NH, methyleneoxy, methyleneamino or methylene (C1–4)-alkylamino Y is O or NH, and drug is a compound which is linked via a hydroxyl, amino or imino group and has a biological effect, preferably a pharmaceutical agent, particularly preferably an anthracycline which is linked via a hydroxyl or, when p=0, non-3'-amino group, preferably doxorubicin, 4'-epidoxorubicin, 4- or 4'-deoxydoxorubicin or a compound preferably selected from the group comprising etoposides, N,N-bis(2-chloroethyl)-hydroxyaniline, 4-hydroxycyclophosphamide, vindesine, vinblastine, vincristine, terfenadine, terbutaline, fenoterol, salbutamol, muscarine, oxyphenbutazone, salicylic acid, paminosalicylic acid, 5-fluorouracil, 5-fluorocytidine, 5-fluorouridine, methotrexate, diclofenac, flufenamic acid, 4-methylaminophenazone, theophylline, nifedipine, mitomycin C, mitoxantrone, camptothecin, m-AMSA, taxol, nocodazole, colchicine, cyclophosphamide, rachelmycin, cisplatin, melphalan, bleomycin, nitrogen mustard, phosphoramide mustard, quercetin, genistein, erbstatin, tyrphostin, rohitukin derivative ((–)-cis-5,7-dihydroxy-2-(2-chlorophenyl)-8-[4-(3-hydroxy-1-methyl)-piperidinyl]-4H-1-benzopyran-4-one; EP 89119710.5), retinoic acid, butyric acid, phorbol ester, DMSO, aclacinomycin, progesterone, buserelin, tamoxifen, mifepristone, onapristone, N-(4-aminobutyl)-5-chloro-2-naphthalenesulfonamide, pyridinyloxazol-2-one, quinolyl-, isoquinolyloxazol-2-one, staurosporine, ethanolamine, verapamil, forskolin, 1,9-dideoxyforskolin, quinine, quinidine, reserpine, methyl 18-O-(3,5-dimethoxy-4-hydroxybenzoyl)reserpate, lonidamine, buthionine-sulfoximine, diethyl dithiocarbamate, cyclosporin A, azathioprine, chlorambucil, N-(4-trifluoromethylphenyl)- 2-cyano-3-hydroxycrotonamide (WO 91/17748). 15-deoxyspergualine, FK 506, ibuprofen, indomethacin, aspirin, sulfasalazine, penicillamine, chloroquine, dexamethasone, prednisolone, lidocaine, propafenone, procaine, mefenamic acid, paracetamol, 4-aminophenazone, muskosine, orciprenaline, isoprenaline, amiloride, p-nitrophenyl guanidinobenzoate or their derivatives additionally substituted by one or more hydroxyl, amino or imino groups.

Preferred compounds of the formula I are those in which
W is a phenyl radical or a polysubstituted phenyl radical in which the substituents R are, independently or identically, H, methyl, methoxy, carboxyl, methylotycarbonyl, CN, hydroxyl, nitro, fluorine, chlorine, bromine, sulfo, sulfamoyl or (C1–4)-allylsulfamoyl and p is 0 or 1, n is 1 to 4, X is O, NH, methyleneoxy, methyleneamino or methylene (C$_{1-4}$)-alkylamino Y is O or NH, and drug is a compound as described above.

Particularly preferred compounds of the formula I are those compounds in which glycosyl is a poly-, oligo- or monosaccharide, in particular an alpha- or beta-O-glycosidically linked D-glucuronyl, D-glucopyranosyl, D-galactopyranosyl, N-acetyl-D-glucosaminyl, N-acetyl-D-galactosaminyl, D-mannopyranosyl or L-fucopyranosyl radical, W is a phenyl radical or a monosubstituted phenyl radical in which one of the substituents R is methoxy, methyloxycarbonyl, CN, hydroxyl, nitro, fluorine, chlorine, bromine, sulfo or sulfamoyl and the others are hydrogen, X is O, NH, methyleneoxy, methyleneamino or methylene-methylamino and Y is O or NH, and drug is a compound as described above.

Preferred embodiments of the invention are the following:
compound in which the glycosyl radical can be cleaved off by enzymatic hydrolysis, in which the spacer can be spontaneously cleaved off by chemical hydrolysis, in which the drug is a pharmaceutical agent or one of its derivatives obtained by introducing additional hydroxyl, amino or imino groups, which is more hydrophilic than the drug, which leads in vivo to fewer toxic reactions than the drug itself, in which the drug is a pharmacologically active substance, in which the drug is additionally substituted by one or more hydroxyl, amino or imino groups and slows down tumor growth, in which the drug is a standard cytostatic, in which the drug is an antimetabolite, in which the drug is 5-fluorouracil, 5-fluorocytidine, 5-fluorouridine, cytosine arabinoside or methotrexate, in which the drug is a substance which intercalates into DNA, in which the drug is doxorubicin, daunomycin, idarubicin, epirubicin or mitoxantrone, in which the drug inhibits topoisomerase I+II, in which the drug is camptothecin, etoposide or M-AMSA, in which the drug is a tubulin inhibitor, in which the drug is vincristine, vinblastine, vindesine, taxol, nocodazole, colchicine or etoposide, in which the drug is an alkylating agent, in which the drug is cyclophosphamide, mitomycin C, rachelmycin, cisplatin, phosphoramide mustard, melphalan, bleomycin, nitrogen mustard or N,N-bis(2-chloroethyl)-4-hydroxyaniline, in which the drug is neocarcinostatin, calicheamicin, dynemicin or esperamicin A, in which the drug is a compound which inactivates ribosomes, in which the drug is verrucarin A, in which the drug is a tyrosine phosphokinase inhibitor, in which the drug is quercetin, genistein, erbstatin, tyrphostin or rohitukin derivative, in which the drug is a differentiation inducer, in which the drug is retinoic acid, butyric acid, phorbol ester, DMSO or aclacinomycin, in which the drug is a hormone, hormone agonist or hormone antagonist, in which the drug is progesterone, buserelin, tamoxifen, mifepristone or onapristone, in which the drug is a substance which alters the pleiotropic resistance to cytostatics, in which the drug is a calmodulin inhibitor, in which the drug is a protein kinase C inhibitor, in which the drug is a P-glycoprotein inhibitor, in which the drug is a modulator of mitochondrially bound hexokinase, in which the drug is an inhibitor of b-glutamylcysteine synthetase or of glutathione Stransferase, in which the drug is an inhibitor of superoxide dismutase, in which the drug is an inhibitor of the proliferation-associated protein defined by MAb Ki67 in the cell nucleus of cells-undergoing division, in which the drug is a substance which has immunosuppressant effects, in which the drug is a standard immunosuppressant, in which the drug is a macrolide, in which the drug is cyclosporine A, rapamycin, FK 506, in which the drug is azathioprine, methotrexate, cyclophosphamide or chorambual, in which the drug is a substance which has an anuinflammatory effect, in which the drug is a non-steroidal anuinflammatory substance, in which the drug is a slow-acting antirheumatic drug, in which the drug is a steroid, in which the drug is a substance which has antiinflammatory, analgesic or antipyretic effect, in which the drug is a derivative of an organic acid, in which the drug is a non-acidic analgesic/antiinflammatory agent, in which the drug is oxyphenbutazone, in which the drug is a local anesthetic, in which the drug is an antiarrhythmic, in which the drug is a Ca++ antagonist, in which the drug is an antihistaminic, in which the drug is an inhibitor of phosphodiesterase, in which the drug is a parasympathomimetic, in which the drug is a sympathomimetic or in which the drug is a substance with an inhibitory effect on human urokinase; and moreover compound in which the glycosyl radical is an alpha- or beta-O-glycosidically linked D-glucuronyl, D-glucopyranosyl, galactopyranosyl, N-acetyl-glucosaminyl, N-acetyl-D-galactosaminyl, D-mannopyranosyl or L-fucopyranosyl radical, or which is 4'-O-[4-(alpha-D-glucopyranosyloxy)phenylaminocarbonyl]etoposide, 4'-O[4-(beta-D-glucopyranosyloxy)phenylaminocarbonyl]etoposide, 4'-O-[4-(alpha-D-galactopyranosyloxy)phenylaminocarbonyl]etoposide, 4'-O-[4-(beta-D-glucuronyloxy)phenylaminocarbonyl]etoposide, 4'-O[4-(beta-D-glucuronyloxy)-3-nitrobenzylaminocarbonyl]etoposide, 4'-4-[(beta-D-glucuronyloxy)-3-chlorobenzylaminocarbonyl]etoposide, 1-N-[4(beta-D-glucuronyloxy)benzyloxycarbonyl]mitomycin C, 14-O-[-beta-D-glucuronyloxy)-3-nitrobenzylaminocarbonyl] doxorubicin, 4-O-[4-(beta-D-glucuronyloxy)benzylaminocarbonyl]-4-hydroxy-N,N-bis(2-chloroethyl) aniline, 4-O-[4-(beta-D-glucuronyloxy)benzylaminocarbonyl]terfenadine, 3'-(4-(beta-D-glucuronyloxy)benzylaminocarbonyaterbutaline, 3'-O-[4-(beta-D-glucuronyloxy)benzylaminocarbonyl]fenoterol, 1"-[4-(beta-D-glucuronyloxy)benzylaminocarbonyl] salbutamol, 3-O-[4-(beta-D-glucuronyloxy) benzylaminocarbonyl]muscarine, 4'-O-[4-(beta-D-glucuronyloxy)benzylaminocarbonyl]oxyphenbutazone, 2-O-[4-(beta-D-glucuronyloxy)benzylaminocarbonyl] salicylic acid, N-[4-(beta-D-glucuronyloxy) benzyloxycarbonyl]diclofenac, N-[4-(beta-D-glucuronyloxy)benzyloxycarbonyl]flufenamic acid, 4-N-[4-(beta-D-glucuronyloxy)benzyloxycarbonyl]4-methylaminophenazone, 7-N-[4-(beta-D-glucuronyloxy) benzyloxycarbonyl]theophylline, 1-N-[4-(beta-D-glucuronyloxy)benzyloxycarbonyl]nifedipine, 4-β-D-glucuronyloxy)-3-nitrobenzyl 2-[1-cyano-1-(N-4-trifluoromethylphenyl)carbamoyl]propen-1-yl carbonate, 3'-N-[4-N-(alpha-D-galactosyloxycarbonyl)-4-aminobenzyloxycarbonyl]doxorubicin, 9-O-[4-(beta-D-glucuronyloxy)-3-chlorobenzyloxycarbonyl]quinine or rhethyl 18-O-[3,5-dimethoxy4-[4-(beta-D-glucuronyloxy)-3-chlorobenzyloxycarbonyl]benzoyl]reserpate.

These compounds can be converted into a suitable pharmaceutical presentation (for example liposomes or with human proteins as carriers) and be used as pharmaceuticals.

The invention also relates to a process for the preparation of a compound of formula I, which comprises reacting a phenyl glycoside of the formula II, prepared as described by Andranomenjanahary et al., Int. Carbohydr. Symposium, p. 299, Abstract A264, Paris, 1992,

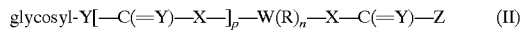

$$\text{glycosyl-Y[—C(=Y)—X—]}_p\text{—W(R)}_n\text{—X—C(=Y)—Z} \quad (II)$$

in which
  glycosyl is a poly-, oligo- or monosaccharde whose hydroxyl groups are free or protected by acetyl or mono-, di- or trihaloacetyl protective groups with halogen being fluorine or chlorine or benzyl protective groups,
  W is an aromatic or heteroaromatic or aliphatic group with conjugated double bonds or an amino-acid derivative radical which cyclizes after elimination of the glycosyl radical, preferably having 5–20 carbon, atoms and 0–4 heteroatoms, where heteroatom means N, O or S, to which the substituents R can be bonded, where
  R are, independently or identically, H, methyl, methoxy, carboxyl, methyloxycarbonyl, CN, hydroxyl, nitro, fluorine, chlorine, bromine, sulfo, sulfamoyl or $(C_{1-4})$-alkylsulfamoyl and
  p is 0 or 1
  n is an integer,
  X is O, NH, methyleneoxy, methyleneamino or methylene $(C_{1-4})$-alkylamino
  Y is O or NH, and
  Z is a reactive leaving group selected from the group comprising chloride, bromide, azide or N-succinimidoxy,
with a drug, preferably as described above, via a reactive hydroxyl, amino or imino group in the presence of an organic base selected from the group comprising triethylamine, diisopropylethylamine or dimethylaminopyridine and a solvent selected from the group comprising acetonitrile, dioxane, tetrahydrofuran, dichloromethane or dichloroethane to give a protected intermediate compound, and subsequently eliminating the protective groups by hydrolysis with alkali metal hydroxide solution, alkali metal carbonate, alkali metal cyanide, barium oxide, piperidine or morpholine in the presence of methanol, ethanol or water, resulting in a compound of the formula I.

The pharmacological activity of glycosyl-spacer-drug compounds according to the invention (called prodrug hereinafter) was tested in vivo in relevant animal experimental systems. The model selected for the oncological indication was one in which human tumors are transplanted subcutaneously to nude mice and the prodrugs according to the invention are administered i.v. after establishment of the tumor;

The results (Examples 26–28 with tables) show that for tumors with a significant, proportion of disintegrating tumor cells the prodrugs according to the invention are considerably more effective than the standard chemotherapy carried out with the maximum tolerated dose of drug. It is immaterial in this connection whether the disintegration of a significant proportion of tumor cells is brought about by the size of the tumor and the resulting deficient nutrition of parts of the tumor (central necrosis) or is induced by an exogenously administered substance (immunotoxin, irradiation, fusion protein as superior embodiment of an antibody-enzyme conjugate, fusion protein composed of a binding region and of DNAse 1, for example scFVDNAsel, cytostatic etc.) in a treatment step which precedes, takes place in parallel or is employed thereafter. The superior pharmacological activity of the prodrugs according to the invention derives from the following properties:

a) The prodrugs are significantly (>70x) less toxic in vivo than the standard drugs contained in the prodrug.

b) The amount of cytotoxic drug liberated from the prodrug in vivo at the site of activation (tumor) is, under the above experimental conditions, 5–50 p higher than the amount of drug which can be achieved in the tumor by standard i.v. therapy.

c) the amount of drug liberated from the prodrug non-specifically in normal tissues, or the drug concentration in normal tissues caused by potential migration out of drug generated at the tumor is distinctly below the concentrations of drug in normal tissue reached after i.v. administration of standard drugs. This observation supports the data which demonstrate the drastic reduction in the in vivo toxicity of the prodrug by comparison with the drug (a).

d) Plasma pharmacokinetic investigations and urine analyses show that the prodrugs according to the invention are, in healthy animals, excreted very rapidly (t ½=12 min) as uncleaved prodrugs mainly via the kidneys.

These observations led to the conclusion that the prodrugs according to the invention have adequate hydrophilicity which results in mainly extracellular distribution in vivo.

Since the glycosyl portion of the prodrugs according to the invention is selected so that it can be cleaved off only by enzymes which are released locally under pathophysiological conditions, the lipophilic drug can likewise be liberated only at the target tissue and display its cytotoxic effect there.

The superior effect of a prodrug according to the invention with a cytotoxic drug component can be increased by combining it with prodrugs according to the invention with a different cytotoxic drug component. In this case, advantageous prodrug combinations are those in which the activity mechanism differs for the cytotoxic components used, corresponding to polychemotherapy. It appears particularly suitable to use drugs which very efficiently cause single-strand and double-strand breaks in the DNA, such as calicheamicin. However prodrug combinations according to the invention which are particularly advantageous are those in which one drug has cytotoxic potential but another, for example, blocks multiple drug resistance. Particularly suitable in this connection are prodrugs according to the invention whose drug component influences multiple drug resistance by inhibiting tyrosine phosphokinase, inducing differentiation, showing a hormonal or hormone-antagonistic effect, being a calmodulin inhibitor, being a protein kinase C inhibitor, being a P glycoprotein inhibitor, being an ion channel blocker, inhibiting mitochondrial hexokinase, or inhibiting gamma-glutamylcysteine synthetase, glutathione S transferase and superoxide dismutase. Other interesting drugs for influencing tumor growth are compounds which functionally block the proliferation-induced protein described by Gerdes et al. (Amer. J. Pathol. 138, 867–873, 1991). Particularly as drug component in the glycosyl-spacer-drug compounds according to the invention it ought to be possible to utilize particularly selectively the efficiency of these drugs after local enzymatic activation.

Particularly beneficial therapeutic effects are achieved when, for example, a glucuronyl-spacer-quinine prodrug is employed in combination with a glucuronyl-spacer-doxorubicin prodrug (see Table 2). Analytical investigations have shown that in a combination of this type the quinine concentration in the tumor is increased to a similarly large extent by comparison with conventional quinine treatment as is the cytostatic drug concentration by comparison with conventional cytostatic therapy.

The following animal experimental systems were selected for the pharmacological testing of prodrugs according to the invention suitable for non-oncological disorders:

a) Granuloma pouch model in the mouse: Bottomley et al., Brit. J. Pharmacol. 93, 627–635 (1988)

b) Adjuvant arthritis in the rat Schorlemmer et al., Expt. Clin. Res. XVII (10/11) 471–483 (1991)

c) DTH model in the mouse Dickneite et al., Infect. Immun. 44(1), 168–174 (1984)

d) Colitis induced by dextran sulfate in the mouse Okayasu et al., Gastroenterology 98, 694–702 (1990)

e) EAE model Schorlemmer et al., Drugs Exptl. Clin. Res. XVII (10/11) 461–469 (1991)

f) MRL-1 model Schorlemmer et al., Int. J. Immunother. VII(4) 169–180 (1991)

The activity in particular of the prodrug compound 8 or 23 described in detail in Example 8 and 22 was investigated in these models. A superior activity of prodrug 22 by comparison with the active substance (Leflunomide) itself was found in particular for adjuvant arthritis and for EAE. A superior effect of prodrug 8 by comparison with standard therapy was found for DTH. In a similar manner to the preceding investigations in the oncological indication, the superior activity was associated with higher concentrations of drugs, especially in the synovial fluid (adjuvant arthritis).

These observations in the non-oncological models mentioned above suggest that the prodrugs according to the invention have general utilizability. Suitable drug components are all substances whose therapeutic use is associated with unpleasant side effects or whose effective concentration is only marginally reached in vivo. These include, besides the immunosuppressant active substance from Example 22, other immunosuppressants (azathioprine, methotrexate, cyclophosphamide, chlorambucil, 15-Deoxyspergualin, cyclosporin A, FK 506 etc.), non-steroidal antiinflammatory drugs (NSAIDs; examples: ibuprofen, indomethacin, aspirin etc.), slow acting antirheumatic drugs (SAARDs: examples: sulfasalazine, penicillamine, chloroquine) and steroids (examples: dexamethasone, prednisolone, etc.). Furthermore suitable as drug component in the prodrugs according to the invention are the substances with antiinflammatory, analgesic and antipyretic effects which are mentioned by way of example hereinafter.

Examples of substances with antiinflammatory, analgesic and antipyretic effects:

1. Derivatives of organic acids:
   salicylic acid
   paminosalicylic acid
   diclofenac
   flufenamic acid
   mefenamic acid
2. Non-acid analgesic/antiinflammatory agents
   paracetamol
   pyrazolone derivatives (for example 4-aminophenazone; 4-methylaminophenazone)
3. oxyphenbutazone.

Other drugs which are suitable as component of the prodrugs according to the invention are the Ca++ antagonists (example: nifedipine, indication: inflammatory disorders), the antihistamines (example: terfenadine, indication: allergy, asthma, inflammatory disorders), inhibitors of phosphodiesterase (example: theophylline, indication: asthma, allergy, inflammatory disorders), parasympathomimetics (example: muscarine, indication: autoimmune diseases) and sympathomimetics (examples: terbutaline, fenoterol, sulbutamol, orciprenaline, isoprenaline, indication: asthma). A class of substances which is particularly suitable as drugs for the prodrugs according to the invention is represented by the synthetic urokinase inhibitors (such as, for example, p-nitrophenyl guanidinobenzoate, amiloride etc.), which might preferably be used in future in prodrug form for the treatment of inflammatory disorders.

In summary, it should be emphasized here once again that the abovementioned drugs and the prodrugs which can be prepared therefrom according to the invention only represent examples. The prodrugs according to the invention can be employed for all non-oncological disorders in which macrophages, granulocytes and platelets occur, especially in the activated state. In the activated state the abovementioned cells mainly secrete intracellular enzymes which makes site-specific activation of the prodrugs according to the invention possible.

In the oncological indication, the activation of the prodrugs according to the invention is brought about by intracellular enzymes released from dying tumor cells. This phenomenon occurs especially with larger tumors (>0.3 cm) but also after damage to the-tumor by treatment with immunotoxins, cytostatics, irradiation, fusion proteins, antibody-enzyme conjugates etc. Furthermore,. it is not possible to rule out a contribution to prodrug activation from activated cells present in the tumor (especially macrophages, granulocytes etc.).

The following examples illustrate the invention:

EXAMPLE 1

4'-O-[4-(Alpha-D-glucopyranosyloxy) phenylaminocarbonyl]etoposide (compound 1)

500 mg (0.68 mmol) of 2",3"-di-O-chloracetyletoposide were dissolved in 50 ml of DMF and, at room temperature, 0.34 ml (3 eq) of diisopropylethylamine and 0.12 ml (1.5 eq) of diphosgene were added. The reaction mixture was stirred for 2 h and subsequently 0.22 ml of diisopropylethylamine and 250 mg (0.9 mmol) of 4-(alpha-D-glucopyranosyloxy) aniline dissolved in 50 ml of DMF were added. The reaction mixture was stirred at room temperature for 14 h, then ethyl acetate was added, and the mixture was washed three times with citrate buffer (pH 5). The organic phase was dried over sodium sulfate and evaporated in vacuo. The residue was purified by column chromatography on silica gel (50 g) with chloroform and methanol 6:1. 438 mg of 4'-O-[4-(alpha-D-glucopyranosyloxy)phenylaminocarbonyl]-2",3"-di-O-chloroacetyletoposide were obtained. Analysis by thin-layer chromatography: Rf=0.6 in chloroform and methanol 3:1.

The resulting conjugate (400 mg) was dissolved in 80 ml of methanol, and 3.0 g of Dowex 1×8 ion exchanger were added. The reaction mixture was stirred at room temperature for 4 h, and the resin was filtered off and washed. The filtrate was evaporated in vacuo. The residue was purified on silica gel (50 g) with chloroform, methanol and glacial acetic acid 5:2:2. 256 mg of title compound were obtained. Analysis by thin-layer chromatography: Rf=0.46 in chloroform, methanol and glacial acetic acid 5:2:2.

EXAMPLE 2

4'-O-[4-(Beta-D-glucopyranosyloxy)phenylaminocarbonyl] etoposide (compound 2)

500 mg (0.68 mmol) of 2",3"-di-O-chloracetyletoposide were dissolved in 50 ml of DMF and, at room temperature, 0.34 ml (3 eq) of diisopropylethylamine and 0.12 ml (1.5 eq) of diphosgene were added. The reaction mixture was stirred for 2 h and subsequently 0.22 ml of diisopropylethylamine and 250 mg (0.9 mmol) of 4-(beta-D-glucopyranosyloxy) aniline dissolved in 50 ml of DMF were added. The reaction mixture was stirred at room temperature for 14 h, then ethyl acetate was added, and the mixture was washed three times with citrate buffer (pH 5). The organic phase was dried over sodium sulfate and evaporated in vacuo. The residue was purified by column chromatography on silica gel (50 g) with chloroform and methanol 6:1. 450 mg of 4'-O-[4-(beta-D-glucopyranosyloxy)phenylaminocarbonyl]-2",3"-di-O-chloroacetyletoposide were obtained. Analysis by thin-layer chromatography: Rf=0.56 in chloroform and methanol 3:1.

The resulting conjugate (400 mg) was deblocked in 80 ml of methanol, with 3.0 g of Dowex 1×8 ion exchanger as described in Example 1. 270 mg of title compound were obtained. Analysis by thin-layer chromatography: Rf=0.44 in chloroform, methanol and glacial acetic acid 5:2:2.

EXAMPLE 3

4'-O-[4-(Alpha-D-galactopyranosyloxy) phenylaminocarbonyl]etoposide (compound 3)

500 mg (0.68 mmol) of 2",3"-di-O-chloracetyletoposide were dissolved in 50 ml of DMF and, at room temperature, 0.34 ml (3 eq) of diisopropylethylamine and 0.12 ml (1.5 eq) of diphosgene were added. The reaction mixture was stirred for 2 h and subsequently 0.22 ml of diisopropylethylamine and 250 mg (0.9 mmol) of 4-(alpha-D-galactopyranosyloxy) aniline dissolved in 50 ml of DMF were added. The reaction mixture was stirred at room temperature for 14 h, then ethyl acetate was added, and the mixture was washed three times with citrate buffer (pH 5). The organic phase was dried over sodium sulfate and evaporated in vacuo. The residue was purified by column chromatography on silica gel (50 g) with chloroform and methanol 6:1. 460 mg of 4'-O[4-(alpha-D-galactopyranosyloxyphenylaminocarbonyl]-2",3"-di-chloroacetyletoposide were obtained. Analysis by thin-layer chromatography: Rf=0.46 in chloroform and methanol 3:1.

The resulting conjugate-(420 mg) was deblocked in 80 ml of methanol, with 3.0 g of Dowex 1×8 ion exchanger as described in Example 1. 250 mg of title compound were obtained. Analysis by thin-layer chromatography: Rf=0.41 in chloroform, methanol and glacial acetic acid 5:2:2.

EXAMPLE 4

4'-O-[4-(Beta-D-glucuronyloxy)phenylaminocarbonyl] etoposide (compound 4)

500 mg (0.68 mmol) of 2",3"-di-O-chloracetyletoposide were dissolved in 50 ml of DMF and, at room temperature, 0.34 ml (3 eq) of diisopropylethylamine and 0.12 ml (1.5 eq) of diphosgene were added. The reaction mixture was stirred for 2 h and then 0.22 ml of diisopropylethylamine and 250 mg (0.86 mmol) of 4-(6-O-methyl-beta-D-glucuronyloxy) aniline dissolved in 50 ml of DMF were added. The reaction mixture was stirred at room temperature for 14 h, then ethyl acetate was added, and the mixture was washed three times with citrate buffer (pH 5). The organic phase was dried over sodium sulfate and evaporated in vacuo. The residue was purified by column chromatography on silica gel (50 g) with chloroform and methanol 6:1. 460 mg of 4'-O-[4-(6-methyl-beta-D-glucuronyloxy)phenylaminocarbonyl]-2",3"-di-O-chloroacetyletoposide were obtained. Analysis by thin-layer chromatography: Rf=0.63 in chloroform and methanol 3:1.

The resulting conjugate (400 mg) was deblocked in 80 ml of methanol with 2.0 g of barium oxide. 280 mg of title compound were obtained. Analysis by thin-layer chromatography: Rf=0.24 in chloroform, methanol and glacial acetic acid 5:2:2.

EXAMPLE 5

4'-O-[4-(Beta-D-glucuronyloxy)-3-nitrobenzylaminocarbonyl]etoposide (compound 5)

500 mg (0.68 mmol) of 2",3"-di-O-chloracetyletoposide were dissolved in 50 ml of DMF and, at room temperature, 0.34 ml (3 eq) of diisopropylethylamine and 0.12 ml (1.5 eq) of diphosgene were added. The reaction mixture was stirred for 2 h and then 0.22 ml of diisopropylethylamine and 250 mg (0.80 mmol) of 4-(6-O-methyl-beta-D-glucuronyloxy)-3-nitrobenzylamine dissolved in 50 ml of DMF were added. The reaction mixture was stirred at room temperature for 14 h, then ethyl acetate was added, and the mixture was washed three times with citrate buffer (pH 5). The organic phase was dried over sodium sulfate and evaporated in vacuo. The residue was purified by column chromatography on silica gel (50 g) with chloroform and methanol 6:1. 456 mg of 4'-O-[4-(6-O-methyl-beta-D-glucuronyloxy)-3-nitrobenzylaminocarbonyl]-2",3"-di-O-chloroacetyletoposide were obtained. Analysis by thin-layer chromatography: Rf=0.64 in chloroform and methanol 3:1.

The resulting conjugate (400 mg) was deblocked in 80 ml of methanol with 2.0 g of barium oxide. 320 mg of title compound were obtained. Analysis by thin-layer chromatography: Rf=0.27 in chloroform, methanol and glacial acetic acid 5:2:2.

EXAMPLE 6

4'-O[4-(Beta-D-glucuronyloxy)-3-chlorobenzylaminocarbonyl]etoposide (compound 6)

500 mg (0.68 mmol) of 2",3"-di-O-chloracetyletoposide were dissolved in 50 ml of DMF and, at room temperature, 0.34 ml (3 eq) of diisopropylethylamine and 0.12 ml (1.5 eq) of diphosgene were added. The reaction mixture was stirred for 2 h and then 0.22 ml of diisopropylethylamine and 250 mg (0.80 mmol) of 4-(6-O-methyl-beta-D-glucuronyloxy)-3-chlorobenzylamine dissolved in 50 ml of DMF were added. The reaction mixture was stirred at room temperature for 14 h, then ethyl acetate was added,. and the mixture was washed three times with citrate buffer (pH 5). The organic phase was dried over sodium sulfate and evaporated in vacuo. The residue was purified by column chromatography on silica gel (50 g) with chloroform and methanol 6:1. 430 mg of 4'-O[4-(6-O-methyl-beta-D-glucuronyloxy)-3-chlorobenzylamino-carbonyl]-2",3"-di-O-chloroacetyletoposide were obtained. Analysis by thin-layer chromatography: Rf=0.68 in chloroform and methanol 3:1.

The resulting conjugate (400 mg) was deblocked in 80 ml of methanol with 2.0 g of barium oxide. 340 mg of title compound were obtained. Analysis by thin-layer chromatography: Rf=0.29 in chloroform, methanol and glacial acetic acid 5:2:2.

EXAMPLE 7

1-N-[4-(Beta-D-glucuronyloxy)benzyloxycarbonyl] mitomycin C (compound 7)

500 mg (1.13 mmol) of 4-(6-methyl-2,3,4-tri-O-acetyl-beta-D-glucuronyloxy)benzyl alcohol were dissolved in 20 ml of toluene, and 440 mg (3 eq) of diisopropylethylamine and 315 mg (1.5 eq) of diphosgene were added. The mixture was stirred at room temperature for 1 h. Subsequently 680 mg (1.8 eq) of mitomycin C and 290 mg (2 eq) of diisopropylethylamine dissolved in 50 ml of DMF were added. The reaction mixture was stirred for 14 h, then ethyl acetate was added, and the mixture was washed with citrate buffer. The organic phase was dried over sodium sulfate and evaporated in vacuo. Crude yield: 651 mg (72%). The conjugate (600 mg) was dissolved in 30 ml of chloroform and methanol 2:1, and 250 mg of barium oxide were added. After stirring for 4 h, the mixture was filtered and the filtrate was evaporated. The residue was purified by column chromatography on Sephadex with methanol and water. Yield of title compound: 335 mg (75%).

EXAMPLE 8

14-O-[4(Beta-D-glucuronyloxy)-3-nitrobenzylaminocarbonyl]doxorubicin (compound 8)

400 mg (0.52 mmol) of 3'-N-fluorenylmethyloxycarbonyldoxorubicin were dissolved in 20 ml of toluene, and 200 mg (3 eq) of diisopropylethylamine and 144 mg (1.5 eq) of diphosgene were added. The reaction mixture was stirred at room temperature for 1 h, and 294 mg (1.8 eq) of 4-(6-O-methyl-beta-D-glucuronyloxy)-3-nitrobenzylamine and 134 mg (2 eq) of diisopropylethylamine dissolved in 50 ml of DMF were added. The mixture was stirred for 14 h, then ethyl acetate was added, and the mixture was washed with citrate buffer (pH 5). The organic phase was dried over sodium sulfate and concentrated in vacuo. The crude product was purified by column chromatography on silica gel. Yield: 370 mg (65%). The protected intermediate compound (300 mg) was dissolved in 20 ml of THF, and 1.0 ml of piperidine was added. The mixture was stirred for 14 h and then evaporated in vacuo and codistilled with toluene. The residue was dissolved in 20 ml of methanol, and 250 mg of barium oxide were added. After stirring for 5 h, the reaction mixture was filtered, and the filtrate was evaporated in vacuo. The residue was purified by column chromatography on Sephadex with methanol and water. Yield of title compound: 140 mg (56%).

EXAMPLE 9

4-O-[4-(Beta-D-glucuronyloxy)benzylaminocarbonyl]-4-hydroxy-N,N-bis(2-chloroethyl)aniline (compound 9)

400 mg (171 mmol) of 4-hydroxy-N,N-bis(2-chloroethyl) aniline were dissolved in 20 ml of toluene, and 950 mg of diisopropylethylamine and 500 mg (1.5 eq) of diphosgene were added. The reaction mixture was stirred for 1 h and then 960 mg (1.8 eq) of 4-(6methyl-beta-D-glucuronyloxy) benzylamine and 0.63 ml of diisopropylethylamine dissolved in 50 ml of DMF were added. The reaction mixture was stirred for 14 h, then ethyl acetate was added, and the mixture was washed with citrate buffer. The organic phase was dried over sodium sulfate and evaporated in vacuo. The residue (550 mg) was dissolved in methanol, and 400 mg of barium oxide were-added. The reaction mixture was stirred for 4 h, filtered and evaporated in vacuo. The residue, was purified by column chromatography on Sephadex. Yield of title compound: 420 mg.

EXAMPLE 10

4-[(4-(Beta-D-glucuronyloxy)benzylaminocarbonyl] terfenadine (compound 10)

The title compound was prepared as described in Example 9 starting from terfenadine and 4-(6-O-methyl-beta-D-glucuronyloxy)benzylamine.

EXAMPLE 11

3'-O-[4-(Beta-D-glucuronyloxy)benzylaminocarbonyl] terbutaline (compound 11)

The title compound was prepared as described in Example 9 starting from terbutaline and 4-(6-methyl-beta-D-glucuronyloxy)benzylamine.

EXAMPLE 12

3'-O-[4-(Beta-D-glucuronyloxy)benzylaminocarbonyl] fenoterol (compound 12)

The title compound was prepared as described in Example 9 starting from fenoterol and 4-(6-methyl-beta-D-glucuronyloxy)benzylamine.

EXAMPLE 13

1"-O-[4-(Beta-D-glucuronyloxy)benzylaminocarbonyl] salbutamol (compound 13)

The title compound was prepared as described in Example 9 starting from salbutamol and 4-(6-methyl-beta-D-glucuronyloxy)benzylamine.

EXAMPLE 14

3-O-[4-(Beta-D-glucuronyloxy)benzylaminocarbonyl] muscarine (compound 14)

The title compound was prepared as described in Example 9 starting from muscarine and 4-(6-methyl-beta-D-glucuronyloxy)benzylamine.

EXAMPLE 15

4'-O-[4-(Beta-D-glucuronyloxy)benzylaminocarbonyl] oxyphenbutazone (compound 15)

The title compound was prepared as described in Example 9 starting from oxyphenbutazone and 4-(6-O-methyl-beta-D-glucuronyloxy)benzylamine.

EXAMPLE 16

2-O-[4-(Beta-D-glucuronyloxy)benzylaminocarbonyl] salicylic acid (compound 16)

The title compound was prepared as described in Example 9 starting from methyl salicylate and 4(6-O-methyl-beta-D-glucuronyloxy)benzylamine.

EXAMPLE 17

N-[4-(Beta-D-glucuronyloxy)benzyloxycarbonyl] diclofenac (compound 17)

The title compound was prepared as described in Example 7 starting from 4-(6-methyl-2,3,4-tri-O-acetyl-beta-D-glucuronyloxy)benzyl alcohol and diclofenac.

EXAMPLE 18

N-[4-(Beta-D-glucuronyloxy)benzyloxycarbonyl] flufenamic acid (compound 18)

The title compound was prepared as described in Example 7 starting from 4-(6methyl-2,3,4tri-O-acetyl-beta-D-glucuronyloxy)benzyl alcohol and flufenamic acid.

EXAMPLE 19

4-N-[4(Beta-D-glucuronyloxy)benzyloxycarbonyl]-4-methylaminophenazone (compound 19)

The title compound was prepared as described in Example 7 starting from 4-(6methyl-2,3,4-tri-O-acetyl-beta-D-glucuronyloxy)benzyl alcohol and 4-methylaminophenazone.

EXAMPLE 20

7-N-[4-(Beta-D-glucuronyloxy)benzyloxycarbonyl] theophylline (compound 20)

The title compound was prepared as described in Example 7 starting from 4-(6methyl-2,3,4-tri-O-acetyl-beta-D-glucuronyloxy)benzyl alcohol and theophylline.

EXAMPLE 21

1-N-[4-(Beta-D-glucuronyloxy)benzyloxycarbonyl] nifedipine (compound 21)

The title compound was prepared as described in Example 7 starting from 4-(6-methyl-2,3,4-tri-O-acetyl-beta-glucuronyloxy)benzyl alcohol and nifedipine.

EXAMPLE 22

4(β-D-Glucuronyloxy)-3-nitrobenzyl 2-[1-cyano-1-(N-4-trifluoromethylphenyl)carbamoyl]propen-1-yl carbonate (compound 22)

The chloroformic ester (4-[(2,3,4-tri-O-acetyl-β-D-glucopyranosyl)methyluronate]-3-nitrobenzyloxycarbonyl chloride) can be prepared by known methods, for example from methyl (4-hydroxymethyl-2-nitrophenil-2,3,4-tri-O-acetyl-β-D-glucopyranoside)uronate and phosgene. Methyl (4-hydroxymethyl-2-nitrophenyl-2,3,4-tri-O-acetyl-β-D-glucopyranoside)uronate can be obtained from methyl (2,3,4-tri-O-acetyl-β-D-glucopyranosyl)uronate bromide by reaction with 2-hydroxy-5-nitrobenzaldehyde and subsequent reduction.

2-Cyano-3-hydroxy-N-(trifluoromethylphenyl) crotonamide is the active metabolite of leflunomide, the hydroxycrotonamide derivative 2 (WO 91/17748). It is obtained according to Example 4B described therein by alkaline ring-opening of leflunomide. 5.5 g (0.091 mol) of 4-[(2,3,4-tri-O-acetyl-β-D-glucopyranosyl)methyluronate]-3-nitrobenzyloxycarbonyl chloride and 2.7 g (0.01 mol) of 2-cyano-3-hydroxy-N(trifluoromethylphenyl)crotonamide are dissolved in 80 ml of acetonitrile. Addition of 1.7 g (0.01 mol) of AgNO3 is followed by heating at 60° C. for 3 hours while stirring. The filtrate obtained after cooling and filtering is evaporated to dryness under reduced pressure. The crude product was dissolved in 200 ml of chloroform/methanol 2:1 (v:v), and 1.5 g of barium oxide were added. The mixture was stirred for 5 h, and the filtrate obtained after filtration

EXAMPLE 23

N-[4-(Alpha-D-galactopyranosyloxycarbonylamino) benzyloxycarbonyl]doxorubicin (compound 23)

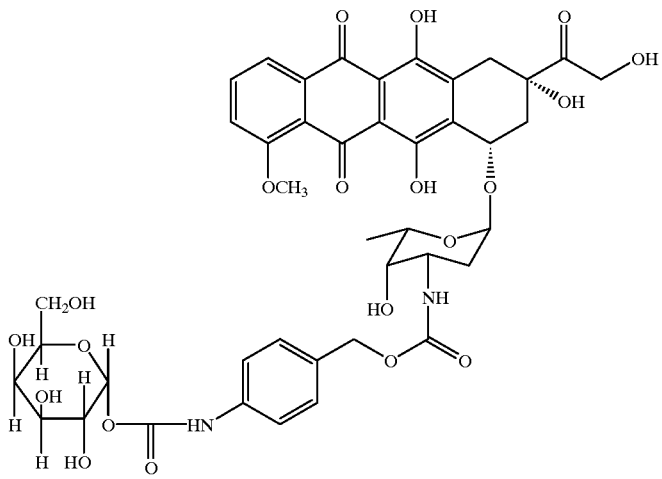

2,3,4,6-Tetra-O-acetyl-D-galactopyranoside (2)

Hydrazine acetate (3.5 g, 38 mmol) was added to a solution of penta-O-acetyl-D-galactose (10 g, 25.6 mmol) in DMF. The mixture was heated at 80° C. for 15 minutes. The cooled solution was diluted with water (100 ml) and extracted with ethyl acetate. The organic phase was washed with brine, dried (MgSO4) and evaporated. Flash chromatography of the residue (cyclohexane:ethyl acetate, 3:2, v/v) resulted in 4.95 g (55%) of compound 2 as solid.

Compound 2: $C_{14}H_{20}O_{10}$, melting point: 104° C. $[\alpha]^{20}_D$+ 95° (C1, CHCl$_3$)

N-[2,3,4,6-Tetra-O-acetyl-α-D-galactopyranosyloxy]-p-toluidine (3)

p-Tolyl isocyanate (4.4 g, 33 mmol) was added to a solution of compound 2 (3.48 g, 10 mmol) in DMF (50 ml). The reaction mixture was stirred at 40° C. for 15 hours and then diluted with H$_2$O (120 ml) and extracted with ethyl acetate. The organic phase was washed first with H$_2$O (2×50 ml) and then with brine, and was dried (MgSO$_4$) and then evaporated under reduced pressure. Flash chromatography (cyclohexane:ethyl acetate, 2:1, v/v) resulted in compound 3 (2.2 g, 45%).

Compound 3: $C_{22}H_{27}O_{11}$ N, melting point: 93° C. $[\alpha]^{20}_D$+84° (C1, CHCl$_3$)

N-(2,3,4,6-Tetra-O-acetyl-α-D-galactopyranosyloxycarbonyl)-4-formylaniline (6) and N-(2,3,4,6-tetra-O-acetyl-α-D-galactopyranosyloxycarbonyl)-4-hydroxymethylaniline (7)

N-Bromosuccinimide (420 mg, 1.1 eq) and 120 mg of benzoyl peroxide were added to a solution of compound 3 (1 g) in CCl$_4$ (60 ml). The mixture was stirred under reflux for 4 hours and then cooled and filtered, and the filtrate was washed with H$_2$O and then with brine and dried (MgSO$_4$). Evaporation under reduced pressure resulted in a residue of 1 g which was purified by flash chromatography and yielded 800 mg of a mixture of monobromo and dibromo compounds. This mixture was directly used further. 800 mg of the mixture were dissolved in acetone (14 ml), and an aqueous solution of silver nitrate (0.1 N, 14 ml) was added. The reaction mixture was stirred at room temperature for 3 hours. The filtrate after filtration through Celite was evaporated under reduced pressure, and the remaining aqueous phase was extracted with CH$_2$Cl$_2$ (dichloromethane). The organic phase was washed with H$_2$O and brine, dried (MgSO$_4$) and evaporated under reduced pressure. The resulting residue was purified by flash chromatography (cyclohexane:acetone, 2:1, v/v) and yielded 120 mg of compound 6 and 260 mg of compound 7.

Compound 6: $C_{22}H_{25}O_{12}N$, melting point: 81° C. $[\alpha]^{20}_D$+ 109° (C1, CHCl$_3$)

Compound 7: $C_{22}H_{27}O_{12}H$, melting point: 85° C. $[\alpha]^{20}_D$+ 129° (C1, CHCl$_3$)

N-(2,3,4,6-Tetra-O-acetyl-α-D-galactpyranosyloxycarbonyl)-4-nitrophenyloxycarbonyloxymethylaniline (8)

p-Nitrophenyl chloroformate (360 mg) and pyridine (0.18 ml) were added to a solution of compound 7 (300 mg) in CH$_2$Cl$_2$ (30 ml). The reaction mixture was stirred at room temperature for 3 hours and then diluted with H$_2$O (50 ml) and extracted. The combined organic phases were washed with H$_2$O and brine and dried (MgSO$_4$). The residue obtained after evaporation under reduced pressure was purified by flash chromatography (cyclohexanelacetone, 2:1, v/v) and yielded 380 mg (51%) of compound 8.

Compound 8: $C_{29}H_{30}O_{16}N_2$, melting point: 92° C. $[\alpha]^{20}_D$+81° (C1, CHCl$_3$)

N-[4-(2,3,4,6-Tetra-O-acetyl-α-D-galactopyranosyloxycarbonylamino)benzyloxycarbonyl]doxorubicin (9)

100 mg of doxorubicin and 80 μl of triethylamine were added to a solution of compound 8 (100 mg) in DMF. The reaction mixture was stirred at room temperature for 6 h. The residue obtained after evaporation under reduced pressure (1 mm, Δ=50° C.) was purified by flash chromatography and yielded 80 mg (50%) of compound 9.

Compound 9: $C_{50}O_{24}H_{54}N_2$, melting point: 142° C. $[\alpha]_D^{20}$+196° (C1, CHCl$_3$)

Compound 23

20 mg of sodium methanolate were added to a solution of compound 9 (100 mg) in MeOH (methanol) (30 ml). The reaction mixture was stirred for 3 hours and neutralized with Amberlite IRC-50 (H$^+$). The filtrate after filtration was concentrated under reduced pressure and yielded a solid residue. Flash chromatography on silica (acetonitrile:water, 9:1, v/v) of this residue yielded 67 mg (80%) of compound 23.

Compound 23: $C_{42}H_{46}O_{20}N_2$, melting point: 136° C. $[\alpha]^{20}{}_D$+225° (C 0.1, EtOH)

$^1$H NMR (270 MHz, D2O): δ 1.3 (d, J=6.3H, Me-6); 1.9 and 2.2 (AB, 2H, CH$_2$-2, J=9); 2.8 and 2.9 (AB, 2H, CH$_2$-2, J=20); 3.8 (S, 3H, OCH$_3$); 5.3 (m, 1H, H-1'); 6.0 (d, 1H, J=3.5); 7.1 (d, 1H, J=8, H-3); 7.3 (d, J=8, 1H, H-2); 7.5 (d, 1H, J=8, H-1); 7.8 (m, H-arom).

EXAMPLE 24

9-O-[4-(Beta-D-glucuronyloxy)-3-chlorobenzyloxycarbonyl]quinine (compound 24)

4-β-D-methylglucuronyloxy-3-chlorobenzaldehyde (1)

A solution of 4-(2,3,4-tri-O-acetyl-β-D-methylglucuronyloxy)-3-chlorobenzaldehyde (3.05 g, 6.45 mmol) in 0.1 N methanolic sodium methanolate (50 ml) was stirred at 0° C. for 30 min. The reaction mixture was neutralized by addition of Amberlite IRC 120 H$^+$ ion exchange resin, filtered and evaporated under reduced pressure to yield 4-β-D-methylglucuronyloxy-3-chlorobenzaldehyde (1) as a foam (2.17 g, 97%).

$C_{14}H_{15}C_{18}$, M=346.5

IR (KBr) ν cm$^{-1}$: 3400, 3030, 2975, 1375, 1040, 835.

$^1$H NMR (300 MHz, (CD$_3$)$_2$SO): 3.25–4.25 (4H, m), 3.70 (3H, s), 5.05 (1 H, d, J=7 Hz), 7.28 (1H, d, J=8 Hz), 7.75(11H, dd, J=8Hz, J=2Hz), 7.90 (1H, d, J=2 Hz), 9.85 (1H, s).

MS (DCl/NH$_3$): m/z: 364/366 (M+NH$_4$)$^+$.

4-(2,3,4-Tri-O-(4-methoxybenzyl)-β-D-methylglucuronyloxy)-3-chlorobenzaldehyde (2)

A solution of 4-β-D-methylglucuronyloxy-3-chlorobenzaldehyde (2.10 g, 6.06 mmol) in dry dimethylformamide (20 ml) was added slowly to a suspension of sodium hydride (2 g) in 20 ml of anhydrous dimethylformamide. 4-Methoxybenzyl chloride (3.2 ml, 23.5 mmol) was added dropwise over 30 min with cooling to keep the reaction mixture at approximately 20° C. The solution was then stirred for 18 h and worked up by addition of methanol (5 ml). After 1 h, the solution was poured into ice and brought to pH 8 with 1 M hydrochloric acid. The aqueous phase was extracted with ethyl acetate (2×50 ml). After washing with water (2×50 ml), the organic phase was evaporated to dryness. Purification of the residue by column chromatography on silica gel 60 H [hexane:ethyl acetate (8:2 v/v)] gave 4-(2,3,4-tri-O-(4-methoxybenzyl)-β-D-methylglucuronyloxy)-3chlorobenzaldehyde (2) as a colorless foam (1.97 g, 46%).

$C_{38}H_{39}ClO_{11}$, M=706.5

IR (KBr) ν cm$^{-1}$: 3040, 2945, 1725, 1505, 1375, 1230, 1040, 825.

$^1$H NMR (300 MHz, (CDCl$_3$): 3.30–4.50 (4H, m), 3.73 (3H, s), 3.85 (3H, s), 3.88 (3H, s), 3.92 (3H, s), 4.50–4.90 (6H, m), 5.12 (1H, d, J=7 Hz), 6.90–7.80 (15H, m), 10.02 (1H, s).

MS (DCl/NH3): m/z: 722/724 (M+NH$_4$)$^+$.

2-Chloro-4-hydroxymethylphenyl 2,3,4-tri-O-(4-methoxybenzyl)-β-D-methylglucuronide (3)

A solution of the aldehyde 2 (1.57 g, 2.22 mmol) in methanol (30 ml) was treated with sodium borohydride (0.7 g) and the reaction mixture was stirred at 0° C. for 90 min. The water-quenched reaction was then extracted with dichloromethane (3×20 ml). Purification by column chromatography on silica gel 60 H [hexane:ethyl acetate (7:3 v/v)] afforded 2-chloro-4-hydroxymethylphenyl 2,3,4-tri-O-(4-methoxybenzyl)-β-D-methylglucuronide (3) as an amorphous solid (1.28 g, 81%).

$C_{38}H_{41}ClO_{11}$, M=708.5

IR (KBr) ν cm$^{-1}$: 3420, 3030, 2935, 1725, 1510, 1510, 1375, 1230, 1040, 825.

$^1$H NMR (300 MHz, CDCl$_3$): 3.25–4.50 (4H, m), 3.69 (3H, s), 3.85 (3H, s), 3.87 (3H, s), 3.91 (3H, s), 4.50–4.80 (8H, m), 5.08 (1H, d, J=7 Hz), 6.85–7.90 (15H, m).

MS (DCl/NH$_3$): m/z: 724/726 (M+NH$_4$)$^+$.

4-2,3,4-Tri-O(4-methoxybenzyl)-β-D-methylglucuronyloxy]-3-chlorobenzyl-4-nitrophenyl carbonate (4)

The alcohol 3 (0.25 g, 0.35 mmol) was dissolved in ethyl acetate (1.5 ml) and pyridine (0.15 ml). 4-Nitrophenyl chloroformate (0.30 g, 1.48 mmol) was added and the resulting mixture was stirred overnight. The solvents were removed under reduced pressure. Purification of the residue by column chromatography on silica gel 60 H [hexane:ethyl acetate (7:3 v/v)] afforded 4-[2,3,4-tri-O-(4-methoxybenzyl)-β-D-methylglucuronyloxy]-3-chlorobenzyl 4-nitrophenyl carbonate. (4) (0.16 g, 52%).

$C_{45}H_{44}ClNO_{15}$, M=873.5

IR (KBr) ν cm$^{-1}$: 3055, 2930, 1735, 1515, 1370, 1320, 1230, 1040, 830.

$^1$H NMR (300 MHz, (CDCl$_3$): 3.25–4.50 (4H, m), 3.71 (3H, s), 3.82 (3H, s), 3.87 (3H, s), 3.91 (3H, s), 4.45–4.85 (6H, m), 5.05 (1H, d, J=7 Hz), 5.15 (2H, s), 6.80–8.40 (19H, m).

MS (DCl/NH$_3$): 891/893 (M+NH$_4$)$^+$.

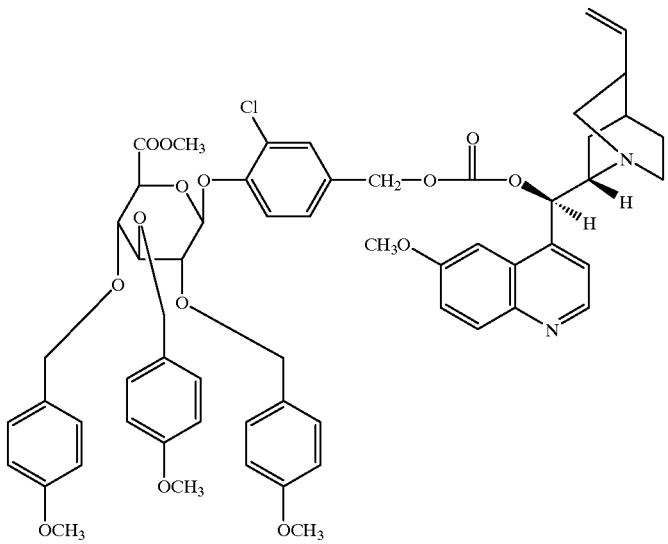

To a stirred solution of 4 (0.15 g, 0.17 mmol) in dichloromethane (20 ml) and triethylamine (188 μl) was added quinine (50 mg, 0.15 mmol). The mixture was kept at room temperature for 18 h. The solvents were evaporated off under reduced pressure. Purification of the residue by column-chromatography on silica gel 60 H [dichloromethane:methanol (95:5 v/v)] gave 5 as a colorless foam (0.057 g, 36%).

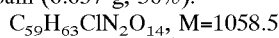

IR (KBr) ν cm$^{-1}$: 3050, 2940, 1740, 1520, 1370, 1320, 1230, 1010, 835, 810.

$^1$H NMR (300 MHz, CDCl$_3$): 1.80–4.40 (15H, m), 3.72 (3H, s), 3.85 (3H, s), 3.93 (6H, s), 3.95 (3H, s), 4.45–4.85 (6H, m), 5.10 (1H, d, J=7 Hz), 5.15 (2H, s), 5.30 (2H, m), 5.72 (1H, m), 6.30 (1H, d, J=7 Hz), 6.80–8.40 (19H, m), 8.75 (1 H, d, J=5 Hz).

MS (DCl/NH$_3$): 1076/1078 (M+NH$_4$)$^+$.

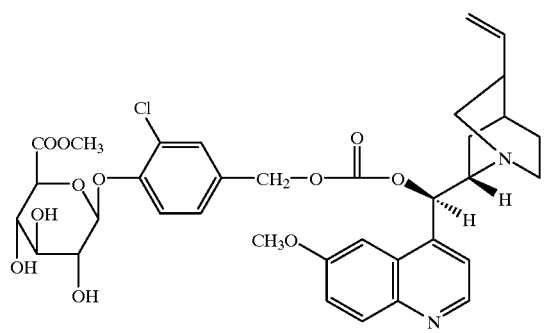

To a stirred solution of 5 (0.050 g, 0.05 mmol) in dichloromethane (10 ml) containing water (0.5 ml) was added 2,3-dichloro-5,6-dicyano-1,4-benzoquinone (0.017 g, 0.075 mmol) at 5° C. After 1 h, saturated aqueous NaHCO$_3$ (10 ml) was added and the mixture was rapidly extracted with dichloromethane (3×15 ml). The organic phase was washed with water, dried over Na$_2$SO$_4$ and evaporated under reduced pressure. The residue was chromatographed on a silica gel 60 H column [dichloromethane:methanol (80:20 v/v)] to give 6 as an amorphous solid (0.023 g, 66%).

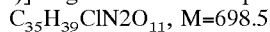

IR (KBr) νcm$^{-1}$: 3420, 3040, 2940, 1735, 1530, 1375, 1320, 1235, 1020, 830.

$^1$H NMR (300 MHz, (CD$_3$)$_2$SO): 1.80–4.30 (15H, m), 3.70 (3H, s), 3.94 (3H, s), 5.12 (1H, d, J=7 Hz), 5.17 (2H, s), 5.30 (2H, m), 5.71 (1H, m), 6.34 (1H, d, J=7 Hz), 7.10–8.00 (6H, m), 8.77(1H,d,J=5Hz).

MS (FAB, matrix: nitrobenzyl alcohol): 699/701 (M+H)$^+$.

Compound 24

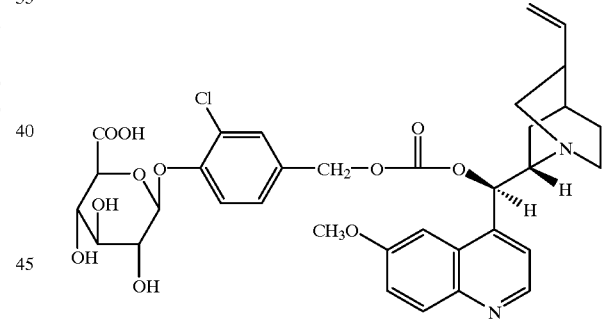

To a solution of 6 (0.020 g, 0.03 mmol) in aqueous phosphate buffer (pH=8) (24 ml) was added pig liver esterase solution (Sigma # E-3128) (0.6 ml) and acetone (12 ml). The mixture was kept for 4 h at 37° C. and evaporated under reduced pressure. Purification of the residue by column chromatography on silica gel 60 H [acetonitrile:water (95:5 v/v)] afforded compound 24 as a colorless solid (0.011 g, 56%).

IR (KBr) ν cm$^{-1}$: 3450, 3060, 2950, 1730, 1520, 1370, 1320, 1240, 1020, 820.

$^1$H NMR (300 MHz, (CD$_3$)$_2$SO): 1.80–4.30 (15H, m), 3.94 (3H, s), 5.10 (1H, d, J=7 Hz), 5.22 (2H, s), 5.32 (2H, m), 5.70 (1H, m), 6.32 (1H, d, J=7 Hz), 7.10–8.00 (6H, m), 8.79 (1H, d, J=5 Hz).

MS (FAB, matrix: nitrobenzyl alcohol): 685/687 (M+H)$^+$.

EXAMPLE 25

Methyl 18-O-[3,5-dimethoxy-4-[4-(beta-D-glucuronyloxy)-3-chlorobenzyloxycarbonyl]benzoyl]reserpate (compound 25)

4-β-D-Glucuronyloxy-3-chlorobenzaldehyde (8)

To a solution of 4-β-D-methylglucuronyloxy-3-chlorobenzaldehyde (1) (3.52 g, 10.1 mmol) in tetrahydrofuran (60 ml) and water (40 ml) was added dropwise 2 M aqueous sodium hydroxide (10 ml) over 30 min. The mixture was stirred for 2 hrs, neutralized by addition of Amberlite IRC 50S H$^+$ ion exchange resin, filtered and evaporated to dryness to give 4-β-D-glucuronyloxy-3-chlorobenzaldehyde (8) as a colorless foam (2.62 g, 78%).

$C_{13}H_{13}ClO_8$, M=332.5

IR (KBr) ν cm$^{-1}$: 3400, 3050, 2940, 1735, 1330, 1040, 830.

$^1$H NMR (300 MHz, (CD$_3$)$_2$SO): 3.25–4.25 (4H, m), 5.05 (1H, d, J=7 Hz), 7.31 (1H, d, J=8 Hz), 7.77 (1H, dd, J=8 Hz, J=2 Hz), 7.92 (1H, d, J=2 Hz), 9.82 (1H, s), 11.85 (1H, br. s).

MS (DCl/NH$_3$); m/z: 350/352 (M+NH$_4$)$^+$.

4-(2,3,4-Tri-O-benzyl)-β-D-benzylglucuronyloxy-3-chlorobenzaldehyde (9)

A solution of 4-(2,3,4-tri-O-benzyl)-β-D-benzylglucuronyloxy-3-chlorobenzaldehyde (9) (2.55 g, 7.67 mmol) in dry dimethylformamide (20 ml) was added slowly to a suspension of sodium hydride (2 g) in 20 ml of anhydrous dimethylformamide. Benzyl bromide (5.0 ml, 42 mmol) was added dropwise over 30 min with cooling to keep the reaction mixture at approximately 20° C. The solution was then stirred for 18 h and worked up by addition of methanol (5 ml). After 1 h, the solution was poured into water and brought to pH 8 with 1 M hydro-chloric acid. The aqueous phase was extracted with ethyl acetate (2×50 ml). After washing with water (2×50 ml), the organic phase was evaporated to dryness. Purification of the residue by column chromatography on silica gel 60 H [hexane:ethyl acetate (85:15 v/v)] gave 4-(2,3,4tri-O-benzyl)-β-D-benzylglucuronyloxy-3-chlorobenzaldehyde (9) as a colorless foam (2.04 g, 38%).

$C_{41}H_{37}ClO_8$, M=692.5

IR (KBr) ν cm$^{-1}$: 3050, 2930, 1730, 1520, 1370, 1330, 1230, 1040, 825.

$^1$H NMR (300 MHz, (CDCl$_3$): 3.40–4.50 (4H, m), 4.50–5.00 (8H, m), 5.08 (1H, d, J=7 Hz), 6.90–7.70 (23H, m), 9.93 (1H, s).

MS (DCl/NH$_3$); m/z: 710/712 (M+NH$_4$)$^+$.

2-Chloro-4-hydroxymethylphenyl 2,3,4-tri-O-benzyl-β-D-benzylglucuronide (10)

A solution of the aldehyde 9 (2.00 g, 2.88 mmol) in methanol (30 ml) was treated with sodium borohydride (0.7 g) and the reaction mixture was stirred at 0° C. for 90 min. The water-quenched reaction was then extracted with dichloromethane (3×20 ml). Purification by column chromatography on silica gel 60 H [hexane:ethyl acetate (7:3 v/v)] afforded 2-chloro-4-hydroxymethylphenyl 2,3,4tri-O-benzyl-β-D-benzylglucuronide (10) as an amorphous solid (1.91 g, 95%).

$C_{41}H_{39}ClO_8$, M=694.5

IR (KBr) ν cm$^{-1}$: 3400, 3040, 2940, 1725, 1515, 1370, 1330, 1230, 1040, 825.

$^1$H NMR (300 MHz, CDCl$_3$): 3.40–4.50 (4H, m), 4.50–5.00 (10H, m), 5.12 (1H, d, J=7 Hz), 6.90–7.75 (23H, m).

MS (DCl/NH$_3$); m/z: 712/714 (M+NH$_4$)$^+$.

4-[(2,3,4-Tri-O-benzyl)-β-D-benzylglucuronyloxy]-3-chlorobenzyl 4-nitrophenyl carbonate (11)

The alcohol 10 (0.40 g, 0.57 mmol) was dissolved in ethyl acetate (2 ml) and pyrdine (0.2 ml). 4-Nitrophenyl chloroformate (0.40 g, 1.97 mmol) was added and the resulting mixture was stirred overnight. The solvents were removed under reduced pressure. Purification of the residue by column chromatography on silica gel 60 H [hexane:ethyl acetate (7:3 v/v)] afforded 4-[(2,3,4-tri-O-benzyl)-β-D-benzylglucuronyloxy]-3chlorobenzyl 4-nitrophenyl carbonate (11) (0.23 g, 47%).

$C_{48}H_{42}ClNO_{12}$, M=845.5

IR (KBr) ν cm$^{-1}$: 3050, 2940, 1735, 1510, 1360, 1320, 1230, 1050, 835, 810.

$^1$H NMR (300 MHz, (CDCl$_3$): 3.40–4.50 (4H, m), 4.55–5.00 (8H, m), 5.12 (1H, d, J=7 Hz), 5.21 (2H, s), 6.80–8.40 (27H, m).

MS (DCl/NH$_3$); m/z: 863/865 (M+NH$_4$)$^+$.

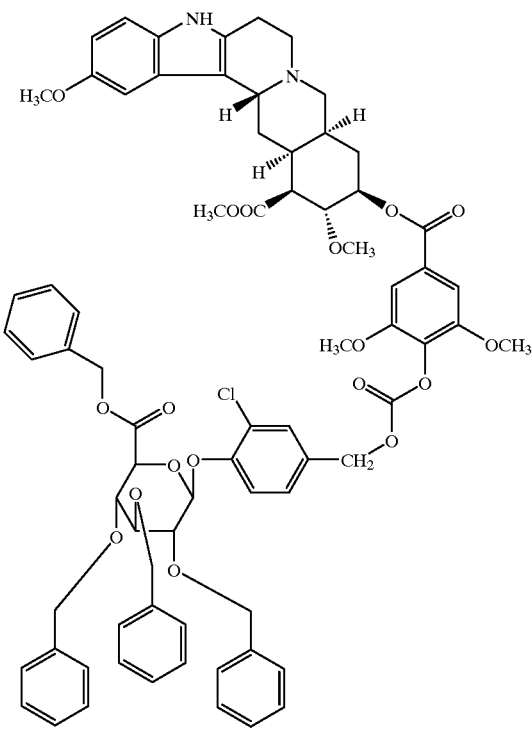

To a stirred solution of 11 (0.20 g, 0.235 mmol) in dichloromethane (20 ml) and triethylamine (260 μl) was added methyl 18-O-(3,5-dimethoxy-4-hydroxybenzoyl) reserpate [Lucas et al., J. Am. Chem. Soc., 1959, 81, 1928–1932] (130 mg, 0.22 mmol). The mixture was kept at room temperature for 22 h. The solvents were evaporated under reduced pressure. Purification of the residue by column chromatography on silica gel 60 H [dichloromethane:methanol (90:10 v/v)] gave 12 as a colorless foam (0.127 g, 44%). $C_{74}H_{75}ClN_2O_{18}$, M=1314.5

IR (KBr) ν cm$^{-1}$: 3050, 2940, 1750, 1720, 1515, 1360, 1320, 1280, 1230, 1050, 835.

$^1$H NMR (300 MHz, (CDCl$_3$): 1.80–4.50 (19H, m), 3.46 (3H, s), 3.80 (3H, s), 3H, s), 3.80 (3H, s), 3.82 (3H, s), 3.97 (6H, s), 4.60–5.00 (8H, m), 5.05 (1H, dd, J=12.9, 5 Hz), 5.14 (1H, d, J=7 Hz), 5.22 (2H, s), 6.70–7.90 (28H, m).

MS (FAB, matrix: thioglycerol): 1315/1317 (M+H)$^+$.

Compound 25

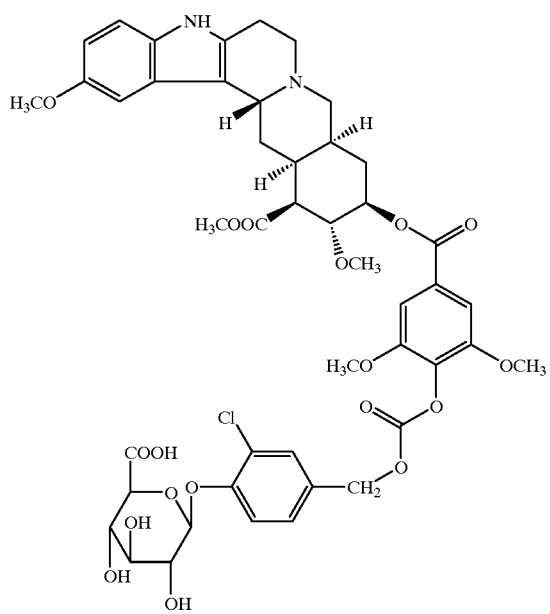

To a solution of 12 (0.100 g, 90.07 mmol) was added palladium (10%) on charcoal (0.2 g), and the resulting mixture was kept under hydrogen (1 atm) for 3 h. The catalyst was removed by filtration through Celite. The filtrate was evaporated under reduced pressure. Purification of the residue by column chromatography on silica gel 60 H [acetonitrile:water (92:8 v/v)] yielded compound 25 as a colorless foam (0.034 g, 51%). $C_{46}H_{51}ClN_2O_{18}$, M=954.5

IR (KBr) ν cm$^{-1}$: 3450, 3650, 2940, 1740, 1725, 1520, 1500, 1360, 1280, 1230, 1050, 825.

$^1$H NMR (300 MHz, (CD$_3$)$_2$SO)): 1.80–4.50 (19H, m), 3.44 (3H, s), 3.79 (3H, s), 3.81 (3H, s), 3.99 (6H, s), 5.04 (1H, dd, J=12.9, 5 Hz), 5.12 (1H, d, J=7 Hz), 5.21 (2H, s), 6.70–7.80 (8H, m).

MS (FAB, matrix: thioglycerol): 955/957 (M+H)$^+$.

The pharmacological activity of the glycosyl-spacer-drug compounds (called prodrug hereinafter) synthesized in Examples 1–25 was tested by way of example in vivo in relevant animal experimental systems. The model selected for the oncological indication was one in which human tumors are transplanted subcutaneously to nude mice and the prodrugs according to the invention are administered i.v. after establishment of the tumor.

EXAMPLE 26

Determination of the acute toxicity:

To determine the acute toxicity, nude mice (CD-1, nu/nu) were infused on day 0 with various doses of the test substance dissolved in 0.5 ml of 5% glucose solution over a period of 5 minutes. Control groups receive merely 0.5 ml of 5% glucose solution. 5 mice are used per concentration of the test substance. The number of mice surviving on day 14 is determined, and the Litchfield Wilcoxon method is used to determine the LD$_{50}$. The toxicity of the investigated prodrug by comparison with the drugs (doxorubicin) is summarized in Table 1.

TABLE 1

| Acute toxicity in nude mice | |
|---|---|
| Substance | LD50 (mg/kg) |
| 14-O-[Beta-D-glucuronyl)-3-nitro-benzylaminocarbonyl]doxorubicin | >1500 |
| Doxorubicin | 20 |

EXAMPLE 27

Inhibition of the growth of human tumors growing subcutaneously in the nude mouse:

The test for the growth-inhibiting activity of the test substances was based on the method described by Fiebig et al (Proc. Europ. Soc. Med. Oncol. in Cancer Chemother. Pharmacol., Suppl. 9, 18, 1982; Verh. dtsch. Ges. inn. Med. 88, 966, 1982) and Inoue et al. (Cancer Chemother. Pharmacol. 10, 182–186, 1983). The tested human tumors are routinely maintained and passaged in nude mice. The tumors are tested for human characteristics by immunohistochemistry using monoclonal antibodies at each 3rd passage. The tumor is removed under sterile conditions and cut into small pieces of about 5–10 mm$^3$. One piece of tumor is implanted subcutaneously into the side of each nude mouse. After about 7–14 days, the piece of tumor is adherent to the surrounding tissue, and the tumor size A is determined with the aid of a calliper rule and measurement of two opposite diameters (a, b) by the following formula:

$$A = a \times b$$

After another measurement of the tumor size carried out at an interval of 3 days, the animals are randomized to the control group and to the groups to be treated (6 animals in each group). Only animals in which a progressive tumor growth was found are used for this. Starting with the day of randomization (day −7), the animals are treated with the test substances in accordance with the scheme indicated below. Twice a week the two tumor diameters are measured for each mouse, and the individual tumor areas are calculated in accordance with the abovementioned formula.

After completion of the experiment, the relative tumor sizes for each individual animal on the particular measurement day are calculated by the formula: $A_r = A_{(day\ x)}/A_{(day\ 0)}$. The median for the treated group (AT) is then related to the median for the relative control tumor size ($A_c$), and T/C %=$A_T/A_C \times 100$ is calculated. The statistical significance of the antitumor effect is determined with the aid of the Wilcoxon U test.

Result:

TABLE 2

| Efficacy for human colon tumors (LoVo) growing subcutaneously in the nude mouse | | | | |
|---|---|---|---|---|
| Substance | Dose (mg/kg) | Treatment scheme | T/C (%) | Significance (p < 0.05) |
| Prodrug* | 500 | 1 × i.v., d0 | 40.0 | + |
| Fusion protein + prodrug* | 30 500 | 1 × i.v., d−7 1 × i.v., d0 | 42.0 | + |
| Doxorubicin | 12 | 1 × i.v., d0 | 78.4 | |

*: 14-O-[4-(Beta-D-glucuronyloxy)-3-nitrobenzylaminocarbonyl] doxorubicin

The animal experimental data presented in Table 2 show that the tumor growth is less fast (T/C~40%) in the animals treated with fusion protein and prodrug or with prodrug alone than the tumor growth (T/C~80%) observed with doxorubicin treatment. The differences between doxorubicin treatment and prodrug therapy, and doxorubicin treatment and fusion protein+prodrug therapy, are statistically significant ($p<0.05$).

Surprisingly, the therapy in the prodrug group was as effective as in the group which received fusion protein in combination with prodrug. It was possible to explain this unexpected observation by the following tissue analyses: histological investigations on cryopreserved LoVo tumors which were taken from tumor-bearing nude mice at the time of the prodrug or doxorubicin therapy (Table 2, d0) showed that the tumors had developed an extensive central necrosis. It was possible to show by means of a histochemical test (Murray et al., the journal of histochemistry and cytochemistry 37, 643–652, 1989) for determining functional human β-glucuronidase that functionally active human p-glucuronidase is present within the necrosis; i.e. cells whose cytoplasmic membrane has already been -damaged still contain functionally active 1-glucuronidase in the cytoplasm. This human β-glucuronidase which is localized in the necrosis and is not protected by the cytoplasmic membrane brings about the cleavage of the hydrophilic prodrug to the drug in the LoVo tumor. This unexpected finding of endogenous activation of the prodrug by the central necrosis was confirmed in a large number of human tumor xenografts (ovarian, breast, stomach, lung and bowel carcinomas). Histological and histochemical investigations on biopsy material from human carcinomas demonstrate that the central necrosis is not an artefact occurring only in human tumors which have undergone xenotransplantation to nude mice but, on the contrary, is a widespread pathophysiological phenomenon which leads to the expectation that prodrug monotherapy in humans has a wide range of possible uses. However, tumors which do not develop a significant proportion of necrosis cannot be treated by prodrug monotherapy (data not shown). In the case of tumors of this type it is absolutely necessary, in order to be able to utilize the superior effect of the prodrug therapy, to use a fusion protein which has previously undergone extracellular localization in the tumor (example: disseminated metastases, small non-necrotic primary tumors etc.).

EXAMPLE 28

Pharmacokinetics of prodrug and doxorubicin in tumor-bearing nude mice

To evaluate the concentrations of prodrug and doxorubicin in tissue and tumor, the prodrug (500 mg/kg) and doxorubicin (10 mg/kg) was infused over a period of 5 min into nude mice which had undergone subcutaneous implantation of a human colon tumor (Mz-Sto-1) 14 days previously. After the infusion the animals were sacrificed at various times, and the organs and the tumor were removed. In each case 770 µl of 20 mM phosphate buffer, 10 mM saccharolactone, pH 3.0, were added to 230 mg of tissue, and the samples were homogenized using an Ultraturrax. 40 µl of 3.3% silver nitrate solution and 160 µl of acetonitrile were added to each 200 µl of this homogenate. After the samples had been shaken for 30 minutes and subsequently centrifuged (5 min, 12,000 g), 100 µl of the supernatant were removed and diluted with 300 µl of phosphate buffer, 10 mM saccharolactonel pH 6.0, and the content of prodrug and doxorubicin was analyzed by means of automatic precolumn extraction on C-18 Bondelut cartridges(AASP)and high-pressure liquid chromatography.

Results:

TABLE 3

Pharmacokinetics of prodrug and doxorubicin in tumor-bearing nude mice

| | | Substance | | |
|---|---|---|---|---|
| | | Prodrug (500 mg/kg) | | Doxorubicin |
| Organ | Time after administration (h) | Prodrug (µg/g) | Doxorubicin (µg/g) | (10 mg/kg) Doxorubicin (µg/g) |
| Tumor | 0.5 | 57.1 | 4.7 | 1.4 |
| Mz-Sto-1 | 1.0 | 69.3 | 11.4 | 2.2 |
| | 4.0 | 12.4 | 16.4 | 1.8 |
| | 8.0 | 3.4 | 9.2 | 1.4 |
| Heart | 0.5 | 68.9 | 4.8 | 9.1 |
| | 1.0 | 83.3 | 5.1 | 10.7 |
| | 4.0 | 5.8 | 4.2 | 14.3 |
| | 8.0 | 0.7 | 3.2 | 5.8 |
| Liver | 0.5 | 131.7 | 11.6 | 23.0 |
| | 1.0 | 165.4 | 13.2 | 23.0 |
| | 4.0 | 27.7 | 8.2 | 17.0 |
| | 8.0 | 6.5 | 6.0 | 9.7 |
| Lung | 0.5 | 156.3 | 6.7 | 12.1 |
| | 1.0 | 186.3 | 10.2 | 15.5 |
| | 4.0 | 7.95 | 9.3 | 21.9 |
| | 8.0 | 0.8 | 5.0 | 15.3 |
| Kidney | 0.5 | 228.9 | 18.2 | 57.0 |
| | 1.0 | 9373.0 | 53.9 | 39.5 |
| | 4.0 | 162.3 | 14.0 | 30.2 |
| | 8.0 | 48.2 | 11.6 | 14.9 |
| Spleen | 0.5 | 47.0 | 6.8 | 19.4 |
| | 1.0 | 89.1 | 9.7 | 4.5 |
| | 4.0 | 9.9 | 13.5 | 4.8 |
| | 8.0 | 0.3 | 7.3 | 3.9 |
| Muscle | 0.5 | 53.0 | 2.0 | 3.5 |
| | 1.0 | 72.9 | 2.9 | 9.6 |
| | 4.0 | 3.8 | 2.7 | 4.7 |
| | 8.0 | 0.6 | 2.0 | 5.2 |

EXAMPLE 29

The effect of 14-O-[4-(beta-D-glucuronyloxy)-3-nitrobenzylaminocarbonyl]doxorubicin (prodrug) on inflammation was investigated in a model of delayed type cutaneous reaction (Delayed Type Hypersensitivity, DTH) corresponding to the method described by Collins and Mackaness (J. Immunol. 101: 830–845, 1968).

In this model, mice were immunized with a defined amount of killed Salmonella typhimurium bacteria (109) twice at an interval of one week. Three weeks after the first immunization a DTH reaction was provoked by intraplantar injection of a Salmonella typhimurium antigen (STA). A local inflammatory infiltrate which was composed of granulocytes, macrophages, lymphocytes and accumulated interstitial fluid developed. The extent of the reaction was measured by the increase in foot swelling 24 hours after provocation of the reaction. The effect of the prodrug on the inflammatory reaction was tested with two treatment schemes. One group received a single intravenous administration of 500 mg/kg prodrug 2 hours after the STA injection, and another group received three injections of, in each case, 300 mg/kg prodrug at times 2, 5 and 8 hours after the STA injection.

As Table 4 shows, both prodrug treatment schemes led to a significant reduction in the inflammatory reaction, and the three administrations of the prodrug were slightly superior to the standard therapy with the antiinflammatory ibuprofen.

TABLE 4

| Group | 24 h foot swelling |
| --- | --- |
| 1. Negative control | 0.82 ± 1.32 |
| 2. Positive control | 10.7 ± 3.4 |
| 3. Prodrug 500 mg/kg, 1 × i.v. (t = +2 h) | 3.5 ± 3.9x |
| 4. Prodrug 300 mg/kg, 3 × i.v. (t = +2, +5, +8 h) | 1.1 ± 1.3xx |
| 5. Ibuprofen 200 mg/kg, 1 × p.o. (t = 0) | 1.7 ± 2.2xx |

EXAMPLE 30

14-O-[4-(Beta-D-glucuronyloxy)-3-nitrobenzylaminocarbonyl]doxorubicin (prodrug) was enclosed in stealth liposomes as described by D. Papahadjopoulos et al. (PNAS, USA 88:11460–11464, 1991). After i.v. injection into CD1 nu/nu mice, the plasma half-life of the prodrug enclosed in liposomes was ≈40 hours which is distinctly longer than the plasma half-life of the free prodrug (≈20 min) (data not shown). This significant increase in t½β led to an improved pharmacological efficacy. A less distinct increase in the plasma half-life was achieved by preincubation of the prodrug with 50 g/l human serum albumin or human acid alpha-1 glycoprotein.

What is claimed is:

1. A method for the treatment of diseases in which intracellular enzymes are released or are made accessible by cell damage, which method comprises administering to a host in need of said treatment an effective amount of a glycosyl-spacer-drug compound;

wherein the glycosyl radical is a mono-, oligo- or polysaccharide which can be cleaved off enzymatically;

wherein the drug is a compound which has antitumor or antiinflammatory or immunosuppressant properties, and the drug contains an OH or $NH_2$ group which is capable of coupling; and wherein the spacer is self-eliminating and is bonded via O or N to the glycosyl radical and via O or N to the drug.

2. The method as claimed in claim 1, wherein the compound is present in a liposome or bound to a carrier protein.

3. The method as claimed in claim 1, wherein the compound is present in combination with a compound which breaks multiple drug resistance.

4. The method as claimed in claim 3, wherein the compound which breaks multiple drug resistance is cyclosporin A, R-verapamil, pentoxifylline or rapamycin.

5. The method as claimed in claim 3, wherein the carrier protein is human serum albumin or human acid alpha-1 glycoprotein.

6. The method as claimed in claim 1 wherein the glycosyl radical is a mono-, oligo- or polysaccharide which is cleaved off by enzymatic hydrolysis and then the spacer is spontaneously cleaved off by chemical hydrolysis.

7. The method as claimed in claim 1 wherein the spacer is an aromatic or heteroaromatic or aliphatic group with conjugated double bonds or an amino-acid derivative which cyclizes after elimination of the glycosyl radical.

8. The method as claimed in claim 1 in which the glycosyl-spacer-drug compound is administered in the form of a pharmaceutical composition also comprising a pharmaceutically acceptable carrier.

* * * * *

UNITED STATES PATENT AND TRADEMARK OFFICE
CERTIFICATE OF CORRECTION

PATENT NO. : 6,146,658  
DATED : November 14, 2000  
INVENTOR(S) : Bosslet et al.

Page 1 of 1

It is certified that error appears in the above-identified patent and that said Letters Patent is hereby corrected as shown below:

<u>Column 28, claim 5,</u>  
Line 17, "claim 3" should read -- claim 2 --.

Signed and Sealed this

Twelfth Day of February, 2002

Attest:

JAMES E. ROGAN  
Attesting Officer     Director of the United States Patent and Trademark Office